US008232419B2

(12) United States Patent
Munson et al.

(10) Patent No.: US 8,232,419 B2
(45) Date of Patent: Jul. 31, 2012

(54) TRIACYLGLYCEROL PURIFICATION BY A CONTINUOUS REGENERABLE ADSORBENT PROCESS

(75) Inventors: James R. Munson, Neshanic Station, NJ (US); Brian S. Cooke, Clarksville, IN (US); Bryan L. Bertram, Floyds Knob, IN (US)

(73) Assignee: The Dallas Group of America, Whitehouse, NJ (US)

( * ) Notice: Subject to any disclaimer, the term of this patent is extended or adjusted under 35 U.S.C. 154(b) by 294 days.

(21) Appl. No.: 12/587,084

(22) Filed: Oct. 1, 2009

(65) Prior Publication Data

US 2010/0087666 A1  Apr. 8, 2010

Related U.S. Application Data

(60) Provisional application No. 61/102,038, filed on Oct. 2, 2008.

(51) Int. Cl.
*C11B 3/00* (2006.01)
(52) U.S. Cl. ..................................................... 554/191
(58) Field of Classification Search .................... 554/191
See application file for complete search history.

(56) References Cited

U.S. PATENT DOCUMENTS

| | | |
|---|---|---|
| 1,745,952 A | 2/1930 | Prutzman |
| 2,093,348 A | 9/1937 | Benedict |
| 2,401,339 A | 6/1946 | Dunmire |
| 2,639,289 A * | 5/1953 | Vogel .............................. 554/191 |
| 3,862,054 A | 1/1975 | Sokolsky et al. |
| 3,955,004 A | 5/1976 | Strauss et al. |
| 4,048,205 A | 9/1977 | Neuzil et al. |
| 4,093,540 A | 6/1978 | Sen Gupta |
| 4,144,373 A | 3/1979 | Weiss et al. |
| 4,664,807 A | 5/1987 | Van Dam et al. |
| 4,770,819 A | 9/1988 | Zinnen |
| 4,781,864 A | 11/1988 | Pryor et al. |
| 4,797,233 A | 1/1989 | Zinnen |
| 4,977,243 A | 12/1990 | Barder et al. |
| 5,157,132 A | 10/1992 | Tan et al. |
| 5,225,560 A * | 7/1993 | Cevasco et al. ............... 546/250 |
| 5,225,580 A | 7/1993 | Zinnen |
| 5,231,201 A | 7/1993 | Welsh et al. |
| 5,248,799 A | 9/1993 | Schmutzler |
| 5,252,762 A | 10/1993 | Denton |

(Continued)

FOREIGN PATENT DOCUMENTS

EP       0295418 B1    12/1988

(Continued)

*Primary Examiner* — Deborah D Carr
(74) *Attorney, Agent, or Firm* — Porzio, Bromberg & Newman, P.C.

(57) ABSTRACT

The process utilizes the adsorbent column system as a treatment after chemical refining or before physical refining rather than water or filtration, respectively, to remove soaps and other impurities entrained in a crude triacylglycerol. The CDTAG or ORTAG is contacted with an adsorbent packed into a column, or multiple columns in series, for a sufficient amount of time to remove impurities such as, but not limited to, soaps, metals, chlorophyll, and many of the other compounds that reduce the stability of the TAG. The resulting TAG exiting the column(s) is ready for the deodorization process. Once the adsorbent no longer removes the desired amount of impurities, it is regenerated for reuse. Such a continuous regenerable adsorbent refining process substantially reduces the amount of fresh water required and the amount of waste water generated to purify TAG and reduces the amount of solid waste produced.

36 Claims, 7 Drawing Sheets

U.S. PATENT DOCUMENTS

| | | | |
|---|---|---|---|
| 5,264,597 A | 11/1993 | Van Dalen et al. | |
| 5,298,639 A | 3/1994 | Toeneboehn et al. | |
| 5,348,755 A | 9/1994 | Roy | |
| 5,401,862 A | 3/1995 | Gonus et al. | |
| 6,229,032 B1 | 5/2001 | Jacobs et al. | |
| 6,248,911 B1 | 6/2001 | Canessa et al. | |
| 6,982,340 B2 | 1/2006 | Mumura et al. | |
| 7,097,770 B2 | 8/2006 | Lysenko et al. | |
| 2003/0176609 A1* | 9/2003 | Oishi et al. | 526/317.1 |
| 2005/0038714 A1 | 2/2005 | Bonet et al. | |
| 2007/0141222 A1* | 6/2007 | Binder et al. | 426/601 |
| 2007/0175092 A1 | 8/2007 | Ames | |
| 2007/0282000 A1 | 12/2007 | Murphy et al. | |

FOREIGN PATENT DOCUMENTS

| | | |
|---|---|---|
| EP | 0507217 A1 | 10/1991 |
| EP | 0566224 A2 | 10/1993 |
| GB | 2058121 A | 4/1981 |
| GB | 2122588 A | 1/1984 |
| JP | 8311480 A | 11/1996 |

* cited by examiner

TRIACYLGLYCEROL PURIFICATION BY A CONTINUOUS REGENERABLE ADSORBENT PROCESS

CROSS REFERENCE TO RELATED APPLICATION

This application claims the benefit of U.S. Provisional Patent Application No. 61/102,038, filed Oct. 2, 2008, the entirety of which is hereby incorporated by reference into this application.

BACKGROUND OF THE INVENTION

1. Field of the Invention

The present invention relates to purification of edible oils and in particular, triacylglycerol, more particularly, to a process for continuous purification of edible oils using an adsorbent material contained in one or more columns and regeneration of the adsorbent material for re-use.

2. Description of the Related Art

Animal and vegetable fats and oils are an essential and popular component of a healthy diet. These oils and fats provide essential nutrients and energy while making many other essential components of a healthy diet more palatable. In 2008 alone, the world-wide consumption of vegetable oils alone was almost 140 million short tons. These oils and fats must be refined in order to remove undesirable impurities that accelerate spoilage and reduce palatability and stability. Impurities to be removed include free fatty acids (FFA), metals, chlorophyll, and phosphatides and gums along with other trace compounds that reduce shelf-life, performance and palatability in the finished oil of fat.

A conventional edible oil refinery uses vast amounts of fresh water to refine its products and produces a corresponding amount of effluent requiring wastewater treatment or disposal into rivers, lakes, or other bodies of water. Additionally, the refinery uses substantial quantities of filter aid or treating media which once used requires disposal by landfill. It is desirable to utilize a process that minimizes the use of fresh water and treating media in order to reduce processing costs, effluent and solid waste.

Oils and fats, which are comprised of triacylglycerols (TAG), must be refined in order to remove undesirable impurities. During the processing of vegetable TAGs, extraction of crude TAG from the oilseed typically involves the use of a non-polar solvent. The conventional solvent most widely used for this process is hexane. Crude TAG is highly soluble in hexane thus allowing for a highly effective extraction of crude TAG from the oilseed. The resulting mixture of crude TAG and hexane can be separated, typically by distillation. The hexane is then recycled for reuse in the solvent extraction process while the crude TAG is further processed and refined by either a "Chemical Refining Process" or a "Physical Refining Process" as described below.

Regardless of the choice of refining method, the TAG should be "degummed" prior to moving forward with the process. The degumming process involves the use of water to remove water soluble phosphatides (gums) from the TAG. The water portion is removed from the TAG by centrifugation. General steps involved for each refining method are described below.

Chemical Refining Process:

A conventional process of chemical refining begins with a crude degummed triacylglycerol (TAG). The crude degummed TAG is subjected to an alkaline solution (typically, sodium hydroxide) to neutralize free fatty acids (FFA) and form a corresponding soap molecule (e.g., sodium oleate). These soaps are removed from the TAG. Centrifugation is used to remove some of the soaps. However, some of the soaps formed during the neutralization are not readily removed by this step and the residual soaps can be removed by further processing.

Residual soaps are removed via different methods. In a first conventional method, water wash is used to remove residual soaps: Since residual soaps are soluble in water, a series of water washing steps can be utilized to remove residual soaps from the TAG. This involves the addition of water to the TAG and soap mixture followed by centrifugation to separate and remove the soap-stock. While this process is efficient for removing the majority of the soaps from the TAG, there are still residual soap molecules remaining in the TAG that must be removed. In addition, there are other impurities present that are not water soluble and thus are not removed using the water washing method. Therefore, further processing of the TAG is required.

In a second conventional method, silica gel treatment using filtration is used to remove soaps from the TAG. The silica gel treatment method has been developed as an attempt to minimize waste effluent streams from the process. A silica gel is added to the TAG to remove soaps and it also removes metals that may be present. This process is highly efficient, but is done in batches, requires filtration, and can produce large amounts of waste filter cake requiring disposal.

Regardless of which conventional chemical refining method is chosen, the next step in the process is a bleaching step. During the bleaching step, the TAG is contacted with a bleaching clay to remove chlorophyll and other impurities that cause stability problems in finished TAG. Bleaching clays are traditionally used for this process due to their efficacy for removing chlorophyll pigments and other trace impurities present in the TAG. Bleaching clays can also remove residual soaps that may not have been removed during the previous processing step. The use of bleaching clay is typically done in batches, requires filtration, and results in large amount of waste filter cake requiring disposal.

The final step in the conventional chemical refining process involves subjecting the refined and bleached TAG to a deodorizing process. The deodorizing process uses steam and vacuum to remove any residual FFA and other volatile impurities that cause odor and color problems in finished TAG. The resulting finished oil from the process is referred to as refined, bleached, deodorized (RBD) TAG.

Conventional chemical refining processes include many variations of the above described methods, such as combining of the silica gel and bleaching clay treatments in one filtration cycle. This allows for faster processing of the TAG. Another conventional process uses a combination of water washing and silica treatment to displace one or more of the water washing steps. Conventional chemical refining of TAGs has the shortcoming of using large amounts of water and generating large amounts of waste effluent and/or solid filter cake waste, depending on the process used.

Physical Refining Process:

The conventional process of physical refining begins with a crude degummed triacylglycerol (TAG). The crude degummed TAG is first subjected to a bleaching clay and/or a silica gel to remove phosphorus compounds and other metals, chlorophyll and other contaminants that cause stability problems in TAGs. The physical refining process generates large amounts of solid filter cake waste that require disposal.

After the bleaching step, the TAG is subjected to the use of steam to remove the majority of FFA present in the TAG. Depending on the condition of the TAG, this step may be performed in a similar fashion to the deodorization step described above in the chemical refining process. If the TAG has a high FFA content, the use of steam to strip the majority of the FFA may be performed prior to a final deodorization step. The final TAG is referred to as refined, bleached, deodorized (RBD) TAG.

Conventional physical refining processes include many variations of the above described process. Conventional physical refining of TAG has the shortcoming of using large amounts of solid filter media and generating large amounts of solid waste requiring disposal.

Typically, whether a chemical refining or physical refining process is chosen depends on the condition of the crude degummed triacylglycerol (CDTAG). CDTAG that contains a high amount of FFA (>1.5%) is typically processed using physical refining. This is primarily because the risk of forming soap emulsion increases as the FFA content of a CDTAG increases. The more soap that is formed in the refining step, the greater the chance of emulsification, which results in increased processing difficulties and higher yield loss.

The following patents describe the use of an adsorbent to remove impurities from triacylglycerol compounds. U.S. Pat. No. 1,745,952 discloses a method for decolorizing fatty substances with adsorbents. U.S. Pat. No. 3,955,004 addresses a process for treating edible glyceride oil to improve color and storage properties using silica and aluminas. U.S. Pat. No. 2,401,339 describes a process to treat oils and waxes to remove impurities through the use of a solid adsorbent and distillation. U.S. Pat. No. 4,781,864 discloses a process for the removal of chlorophyll, color compounds and phospholipids using acid-treated silica type adsorbents.

U.S. Pat. No. 5,231,201, U.S. Pat. No. 5,248,799, U.S. Pat. No. 5,264,597, U.S. Pat. No. 5,928,639, U.S. Pat. No. 6,248,911, European Patent No. 0295418 B1, European Patent No. 0566224 A2, and U.K. Patent No. GB 2058121 A all relate to a process by which a refined glyceride oil is treated with an amorphous silica to remove impurities during chemical and/or physical refining.

U.K. Patent Application No. GB 2122588 A describes a process for regenerating spent adsorbents used for refining fatty materials, comprising contacting the spent adsorbent first with a polar organic solvent to remove adsorbed impurities and then with a non-polar organic displacing agent to remove the solvent adsorbed and reactivate the adsorbent.

None of aforementioned patents describe a complete system employing a continuous purification process using columns in combination with regeneration of the adsorbent. None of the prior art of which applicant is aware provides the feature of a continuous, regenerable adsorbent system that can be used to effectively and economically remove impurities when using chemical or physical refining methods. A purification system employing this feature is desirable in order to conserve and efficiently use scarce resources. Such a system dramatically reduces or eliminates the need for fresh water and the treatment or disposal or effluent and/or solid waste.

It is desirable to eliminate batch processing and provide a continuous process for the purification of edible oils. It is also desirable to provide an environmentally friendly "green" process that greatly reduces or eliminates the large volumes of fresh water conventionally required and waste water produced to refine edible oils and fats, as well as, the energy and space required to produce, transport, and landfill solid waste.

It is further desirable to provide a process that once charged with an adsorbent comprises a closed system requiring no fresh water or new adsorbent for operation while generating no effluent or solid waste that needs to be treated or disposed of.

SUMMARY OF THE INVENTION

The continuous regenerable adsorbent process of the present invention is an environmentally friendly "green" refining process for the continuous purification of TAG using a powdered, granulated, or extruded adsorbent which can be used in conjunction with either chemical or physical refining processes. The adsorbent is contained in a column or suitable filtration system and is regenerated for reuse. The process substantially reduces the need for fresh water, treatment of waste effluent, and disposal of solid waste.

The process utilizes an adsorbent column system as a treatment rather than a conventional water wash step and/or batch filtration step to remove soaps and other impurities entrained in a crude degummed triacylglycerol (CDTAG) in a chemical and/or physical refining process. In the chemical refining process, the CDTAG is first refined to remove FFA, forming a once refined triacylglycerol (ORTAG), and then contacted with an adsorbent packed into column(s) prior to deodorization. In the physical refining process, the CDTAG is contacted with an adsorbent packed into column(s) prior to the removal of FFA and deodorization steps.

The CDTAG or ORTAG is contacted with a sufficient amount of adsorbent and for a sufficient amount of time to remove impurities, such as soaps, metals, chlorophyll, and many of the other impurities that reduce the stability of finished TAG. The life cycle of the adsorbent in the column(s) depends on the level of impurities in the incoming CDTAG or ORTAG, the quantity and adsorptive capacity of the adsorbent in the column(s), and the flow rate of the CDTAG or ORTAG through the column system. TAG so treated results in a product acceptable to proceed into a deodorization step without the need for water washing or batch adsorptive treatment with filtration.

Once the TAG exiting the column(s) no longer meets required parameters for the next step in the process, the adsorbent column(s) in the system are regenerated for reuse. This regeneration of the adsorbent makes the system of the present invention both economical and environmentally friendly. Regeneration and reuse of the adsorbent eliminates large amounts of waste water and/or solid filter cake waste produced in conventional chemical and physical refining processes. The regeneration of the adsorbent, as opposed to disposal of the adsorbent, reduces the production of solid waste. Reclamation by distillation of solvents used in the regeneration process of the present invention further enhances economics of the process and its environmental benefits.

There are several different embodiments that can be used to regenerate the adsorbent depending upon the process being utilized to refine and process the TAG. In a first embodiment which can be used with edible oil purification in either a chemical or physical refining process, the first step in the regeneration of the adsorbent involves reclaiming residual TAG absorbed by the adsorbent with a non-polar solvent (NPS), such as hexane, which is typically used in a solvent extraction process of crude TAG. The NPS is passed through the adsorbent column to strip the absorbed TAG, which is soluble in the NPS, from the adsorbent.

When the system of the present invention is used in an oil seed processing plant, specifically in the oil extraction process, the resulting NPS and TAG mixture exiting the adsorbent column can be added directly into the NPS and TAG from the TAG extraction step in the oil extraction process. The NPS from this first step of the adsorbent regeneration is reclaimed, typically by distillation, for reuse along with the NPS from the solvent extraction of the crude TAG from the oilseed. Alternatively, if there is no upstream TAG extraction step, the NPS and TAG mixture can be separated by distillation and the residual TAG can be sent downstream to the next step in the process for further processing, typically deodorization or FFA steam stripping, and the NPS can be reclaimed and reused in the regeneration process. If the resulting TAG from the separation process does not meet required parameters or specifications it can be sent back upstream to the adsorbent column(s) for reprocessing.

During a second step of the regeneration of the adsorbent, a polar solvent (PS), such as methanol or ethanol, is mixed with an acid, such as sulfuric acid, and is passed through the adsorbent column to remove the adsorbed impurities contained in and on the adsorbent. The PS and acid solution is passed through the column until such time as there are no significant quantities of impurities in the resulting PS and acid solution filtrate. The regenerated adsorbent is then ready to be reused in the purification process. The adsorbent can be reused multiple times until such time as it loses adsorptive capacity or is physically degraded to such an extent that it can no longer be used.

The mixture resulting from the second step of the regeneration process contains PS, acid, alkyl soaps, metals, chlorophyll and other impurities. The PS from the mixture of PS and acid and impurities can be reclaimed for reuse using distillation. The distillation process involves subjecting the mixture of PS and acid and impurities to heat and/or vacuum so that only the PS volatilizes and is then collected and reclaimed for reuse in the adsorbent regeneration process. The remaining residue not volatilized by the distillation process can be either disposed of or, preferably, further processed into a value added product.

In a second embodiment which can be used in a chemical refining process, the regeneration can be accomplished using a single solvent. A polar solvent (PS), such as methanol or ethanol, is mixed with an acid, such as sulfuric acid, and is passed through the adsorbent column to remove impurities contained in and on the adsorbent. The solution of PS and acid is passed through the adsorbent column until such time as there are no significant quantities of impurities in the resulting PS and acid solution filtrate.

The regenerated adsorbent is then ready to be reused in the purification process. The adsorbent can be reused multiple times until such time as it loses adsorptive capacity or is physically degraded to such an extent that it can no longer be used.

The mixture resulting from the regeneration process contains PS, acid, alkyl soaps, metals, chlorophyll, TAG, and other impurities which can be further processed to recover the residual TAG and PS. The PS can be reclaimed for reuse using distillation.

The distillation process involves subjecting the mixture of PS, acid and TAG impurities to heat and/or vacuum so that only the PS volatilizes and is then collected and reclaimed for reuse in the adsorbent regeneration process. The remaining residue not volatilized by the distillation process can be either disposed of or, preferably, further processed to recover the residual TAG.

To recover the residual TAG, the residue not volatilized by the distillation process which contains alkyl soaps, metals, chlorophyll, residual TAG and other impurities can be added back upstream into the process at the point at which the alkaline solution is added to the CDTAG. This CDTAG will then be centrifuged and the impurities from the regeneration process will be separated from the residual TAG. This recovered TAG is combined with the ORTAG after the centrifugation. The recovered TAG then becomes part of the ORTAG which is then further processed by passing through the adsorbent column(s) as described above.

In a third embodiment which can be used in a physical refining process, the regeneration can be accomplished using a single solvent. A polar solvent (PS), such as methanol or ethanol, is passed through the column to remove impurities contained in and on the adsorbent. The PS is passed through the adsorbent column until such time as there are no significant quantities of impurities in the resulting PS filtrate.

The regenerated adsorbent is then ready to be reused in the purification process. The adsorbent can be reused multiple times until such time as it loses adsorptive capacity or is physically degraded to such an extent that it can no longer be used.

The mixture resulting from the regeneration process contains PS, alkyl soaps, metals, chlorophyll, and residual TAG which can be further processed to recover the PS and possibly other constituents. The PS can be reclaimed for reuse using distillation.

The distillation process involves subjecting the mixture of PS, TAG and impurities to heat and/or vacuum so that only the PS volatilizes and is then collected and reclaimed for reuse in the adsorbent regeneration process. The remaining residue not volatilized by the distillation process can be further processed to yield value added products or disposed of.

Regardless of which method is chosen for the regeneration process, after the regeneration process, the adsorbent will still have some residual solvent remaining absorbed in it. The amount of solvent remaining in the column will depend on how well the column is dried after the regeneration process. Once the flow of crude TAG is restarted through the regenerated adsorbent column, residual solvent from the adsorbent will become entrained in the TAG first passing through the column. The TAG exiting the column with entrained solvent may be sent directly to the deodorization step in the refining process, a step that will strip the solvent from the TAG. Alternatively, the TAG exiting the column with entrained solvent may be sent to a separate evaporation step to strip the solvent from the TAG prior to being sent to the deodorization step in the refining process.

The invention will be more fully described by reference to the following drawings.

DETAILED DESCRIPTION

Figure 1:
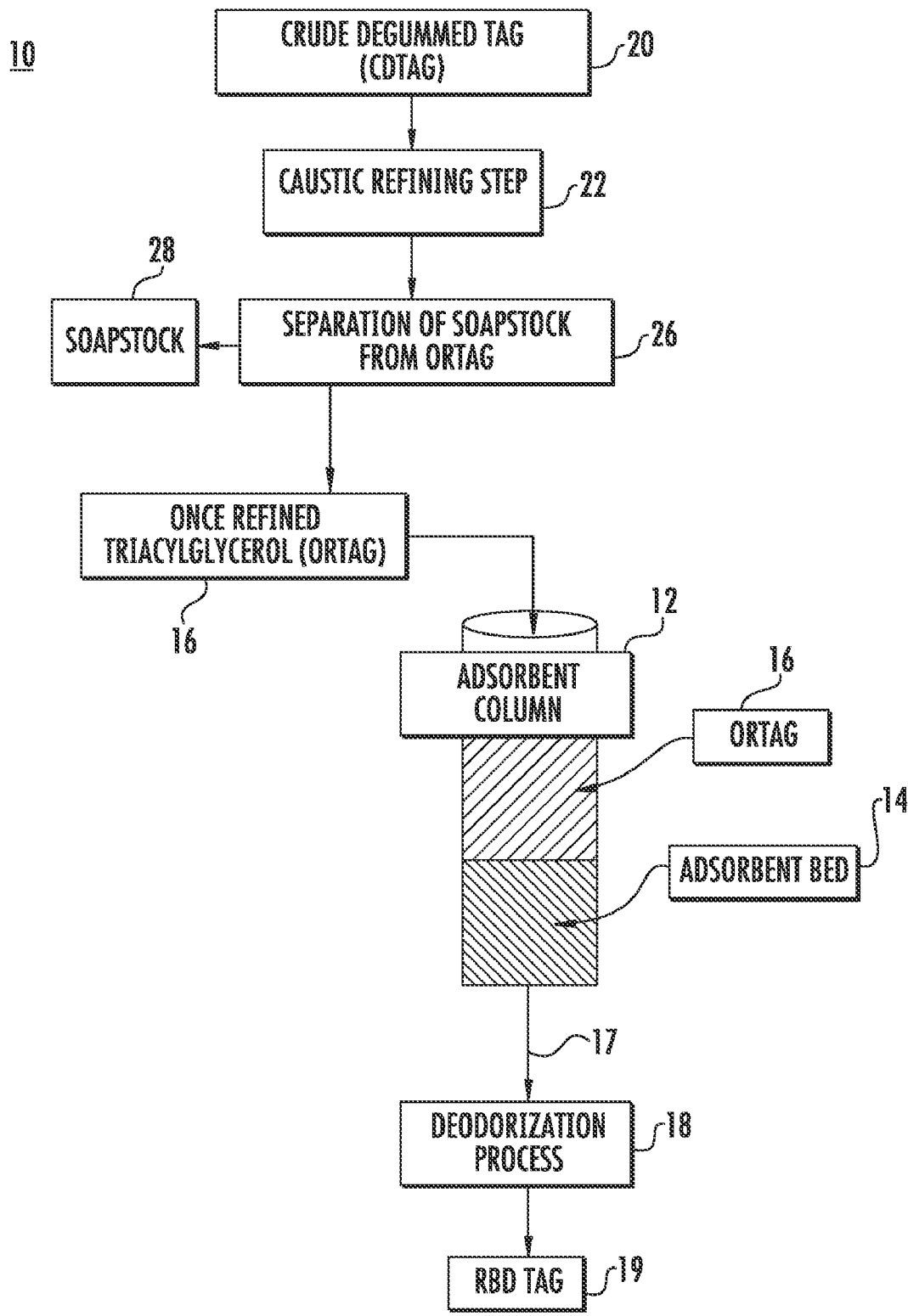
FIG. 1 is schematic diagram of a system for purification of animal and vegetable oils using an adsorbent column purification method in a chemical refining application in accordance with the teachings of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a schematic diagram of continuous edible oil purification by adsorbent system 10 in accordance with the teachings of the present invention. In a first embodiment, single adsorbent column 12 packed with adsorbent material 14 is used to purify once refined triacylglycerol (ORTAG) from a chemical refining process 16. ORTAG 16 is contacted with a sufficient amount of adsorbent material 14 and for a sufficient amount of time to remove impurities, such as soaps, chlorophyll, metals, phosphorous, phosphatides, gums, free fatty acids (FFA), flavor compounds, odor compounds, and color compounds and other impurities that reduce the stability of finished TAG. Suitable adsorbent materials 14 include carbon, silica, zeolite, metal silicate, metal oxide, silica gel, activated alumina, bleaching clay and activated bleaching clay. Adsorbent material 14 can be a powder, granulated or extruded or otherwise processed to facilitate flow through adsorbent column 12. In preferred embodiments, adsorbent material 14 is magnesium silicate, synthetic magnesium silicate, silica gel, activated alumina, bleaching clay or activated bleaching clay.

Purified TAG 17 exiting adsorbent column 12 is suitable to proceed to deodorization process 18 without the need for water washing or a batch adsorptive filtration treatment. Deodorization process 18 can use steam and vacuum to remove any residual FFA and other volatile impurities. Refined, bleached, deodorized (RBD) TAG 19 results from deodorization process 18.

In this embodiment of a chemical refining process, crude degummed TAG (CDTAG) 20 is refined using caustic refining step 22. In caustic refining step 22, CDTAG 20 is subjected to an alkaline solution, for example a solution of sodium hydroxide, for neutralizing free fatty acids and forming a corresponding soap molecule. Separation of soapstock step 26 results in soapstock 28 being removed to provide ORTAG 16. Separation of soapstock step 26 can be performed with centrifugation to remove soapstock 28.

During the column adsorption purification step, ORTAG 16 flows through adsorbent column 12 until such time as adsorbent material 14 no longer removes sufficient impurities from ORTAG 16. This is determined by comparing the level of impurities in ORTAG 16 entering adsorbent column 12 to those in purified TAG 17 exiting adsorbent column 12. At such time as purified TAG 17 exiting adsorbent column 12 no longer meets the required specification or desired parameters, a regeneration of adsorbent material 14 is performed as described below.

Figure 2:
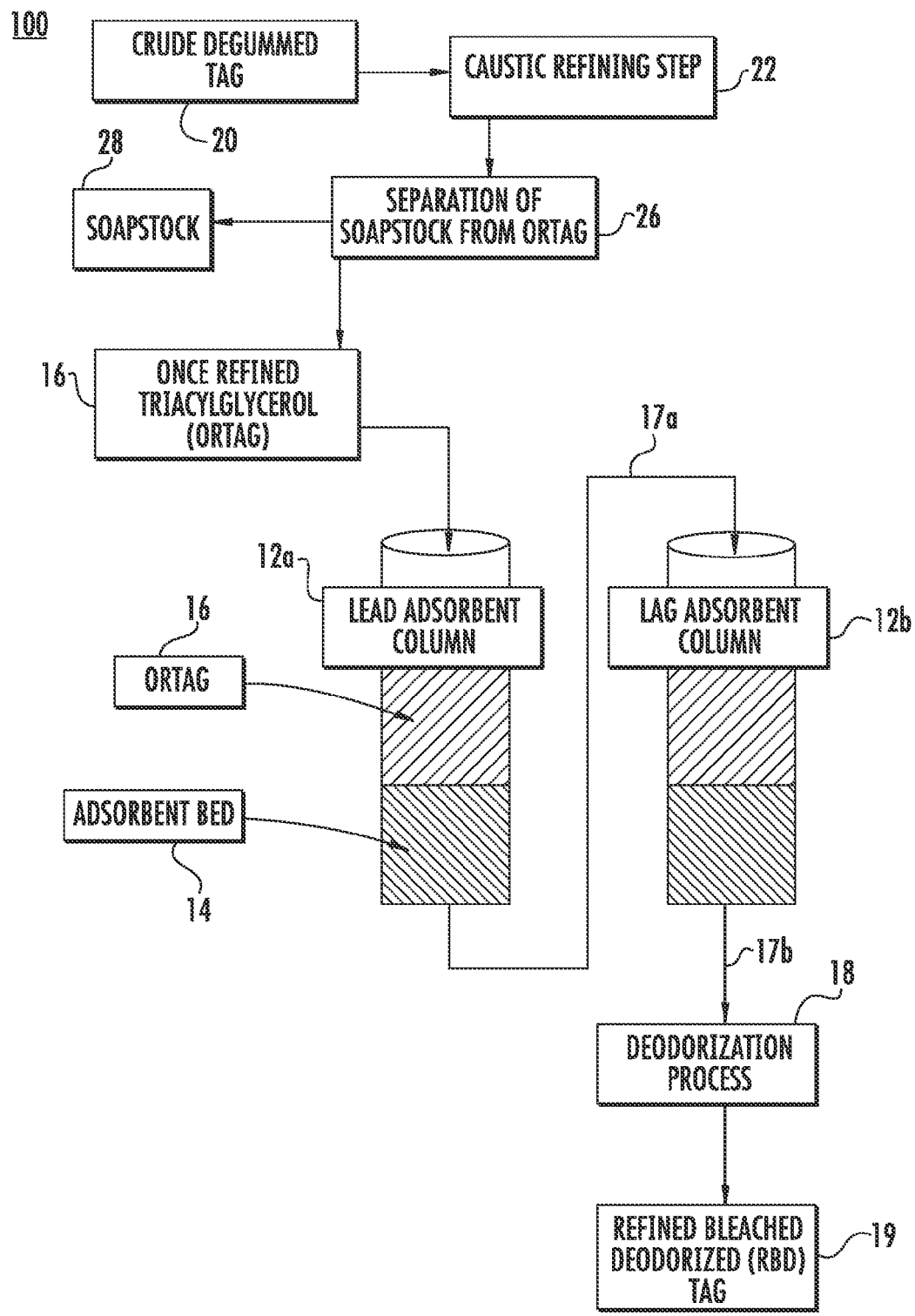
FIG. 2 is a schematic diagram of an alternative embodiment of the system for purification of animal and vegetable oils in a chemical refining application using multiple adsorbent columns is accordance with the teachings of the present invention.

In a second embodiment of continuous edible oil purification by adsorbent system 100, a plurality of adsorbent columns 12a-12b packed with adsorbent material 14 are used in series to purify ORTAG from the chemical refining process 16, as shown in FIG. 2. The use of multiple adsorbent columns allows for a continuous process. After the chemical refining process and separation of soapstock step 26, ORTAG 16 is contacted with adsorbent material 14 in lead adsorbent column 12a. Purified TAG 17a exiting adsorbent column 12a is contacted with adsorbent material 14 in lag adsorbent column 12b packed with adsorbent material 14 to remove impurities remaining in purified TAG 17a.

ORTAG 16 and purified TAG 17a are contacted with a sufficient amount of adsorbent material 14 and for a sufficient amount of time to remove impurities, such as soaps, chlorophyll, metals, and many of the impurities that reduce the stability of finished TAG. ORTAG so treated will result in refined and purified TAG without the need for water washing or batch adsorptive filtration treatment, prior to deodorization process 18.

During the column adsorption purification step, ORTAG 16 and purified TAG 17a flows through the columns until such time as adsorbent material 14 no longer removes sufficient impurities. This is determined by comparing the level of impurities in ORTAG 16 and/or purified TAG 17a entering both lead adsorbent column 12a and lag adsorbent column(s) 12b to those in the purified TAG 17a and purified TAG 17b exiting respective lead adsorbent column 12a and lag adsorbent column 12b. At such time as the purified TAG 17 exiting adsorbent columns 12 no longer meets the required specifications or desired parameters for the next step in the process as determined appropriate for each column, a regeneration of the lead column is performed as described below.

Figure 3:
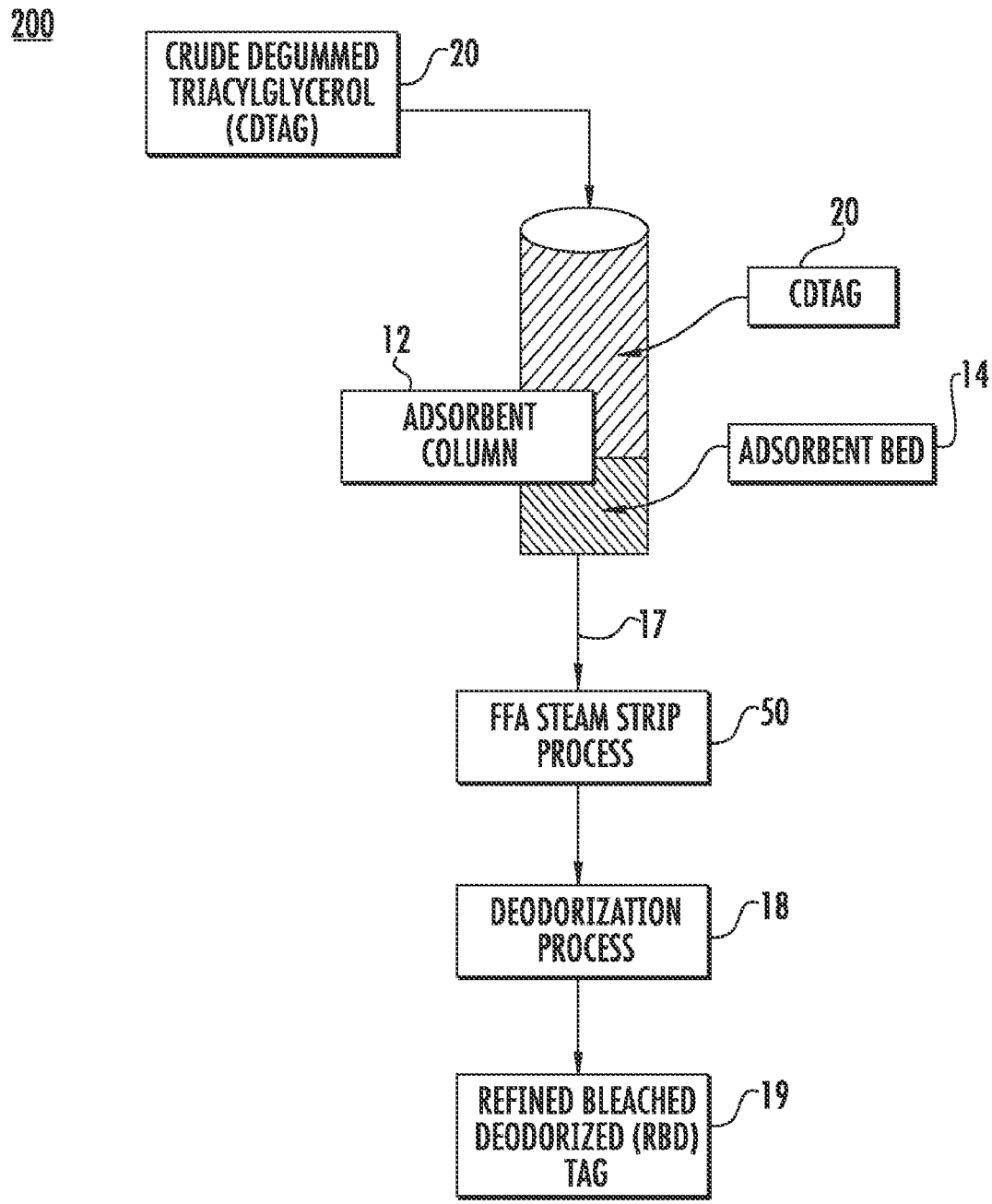
FIG. 3 is a schematic diagram of a system for purification of animal and vegetable oils using an adsorbent column purification method in a physical refining application in accordance with the teachings of the present invention.

In a third embodiment of continuous edible oil purification for a physical refining process by adsorbent system 200, a single adsorbent column 12 packed with adsorbent material 14 is used to purify crude degummed triacylglycerol (CDTAG) 20, as shown in FIG. 3. After the crude TAG is degummed and centrifuged to separate the water soluble gums, such as phosphatides, CDTAG 20 is contacted with a sufficient amount of adsorbent material 14 and for a sufficient amount of time to remove impurities, such as soaps, chlorophyll, metals, and many other impurities that reduce the stability of purified TAG. A CDTAG so treated will result in processed TAG without the need for additional batch adsorptive treatment with filtration. At this point, purified TAG 17 is ready for the steam stripping process 50 to remove the majority of the FFA which is then further processed by deodorization process 18 to provide refined, bleached, deodorized (RBD) TAG 19.

During the column adsorption purification step, CDTAG 20 flows through adsorbent column 12 until such time as adsorbent material 14 no longer removes sufficient impurities from CDTAG 20. This is determined by comparing the level of impurities in CDTAG 20 entering adsorbent column 12 to those in purified TAG 17 exiting adsorbent column 12. At such time as the purified TAG 17 exiting adsorbent column 12 no longer meets the required specification or desired parameters for the next step in the process, a regeneration of adsorbent material 14 is performed. When regeneration is performed, the use of a second column may be employed for the purification process while the first column is being regenerated as described above. This allows for a continuous process.

Figure 4:
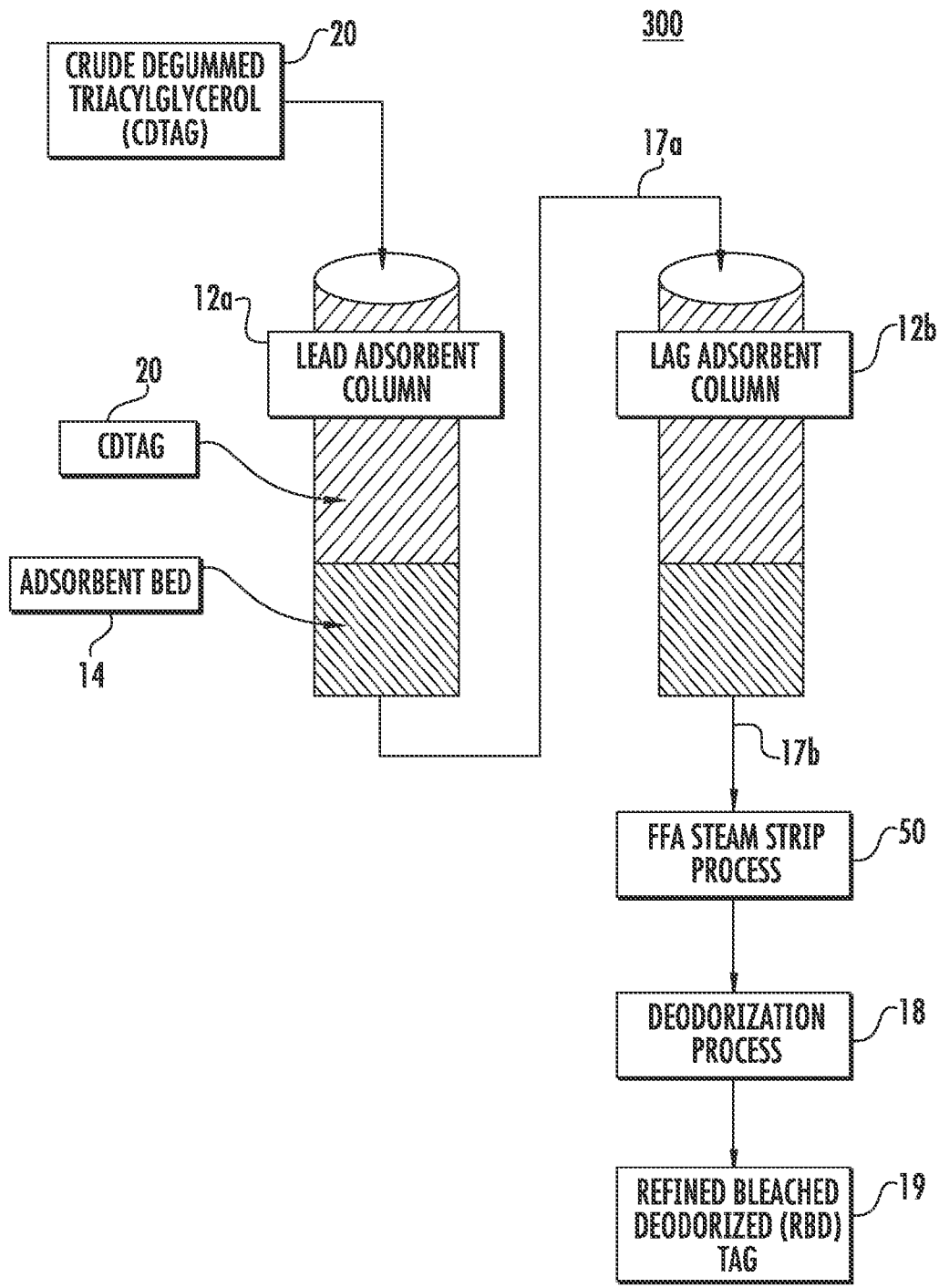
FIG. 4 is a schematic diagram of an alternative embodiment of the system for purification of animal and vegetable oils in a physical refining process using multiple adsorbent columns in accordance with the teachings of the present invention.

In a fourth embodiment, a plurality of adsorbent columns 12a-12b packed with adsorbent material 14 are used in series to purify a crude degummed triacylglycerol (CDTAG) 20 for a physical refining process, as shown in FIG. 4. The use of multiple columns allows for a continuous process. After the crude TAG is degummed and centrifuged to separate the water soluble gums, such as phosphatides, CDTAG 20 is contacted with adsorbent material 14 in lead adsorbent column 12a and lag adsorbent column(s) 14b packed with adsorbent material 14 to intercept impurities from CDTAG 20.

CDTAG 20 is contacted with a sufficient amount of adsorbent and for a sufficient amount of time to remove impurities, such as soaps, chlorophyll, metals, and impurities that reduce the stability of finished TAG. CDTAG so treated will result in processed TAG without the need for additional batch adsorptive treatment with filtration. At this point, purified TAG 17b is ready for the steam stripping process 50 to remove the majority of the FFA which is then further processed by deodorization process 18.

During the column adsorption purification step, CDTAG 20 flows through column 12a and column(s) 12b until such time as the adsorbent no longer removes sufficient impurities from CDTAG 20. This is determined by comparing the level of impurities in CDTAG 20 and/or purified TAG 17a entering both lead adsorption column 12a and lag adsorbent column(s) 12b to those in purified TAG 17a and purified TAG 17b exiting the columns. At such time as the purified TAG 17 exiting the columns 12 no longer meets the required specifications or desired parameters for the next step in the process as determined appropriate for each column, regeneration of the lead column is performed as described below.

Figure 5:
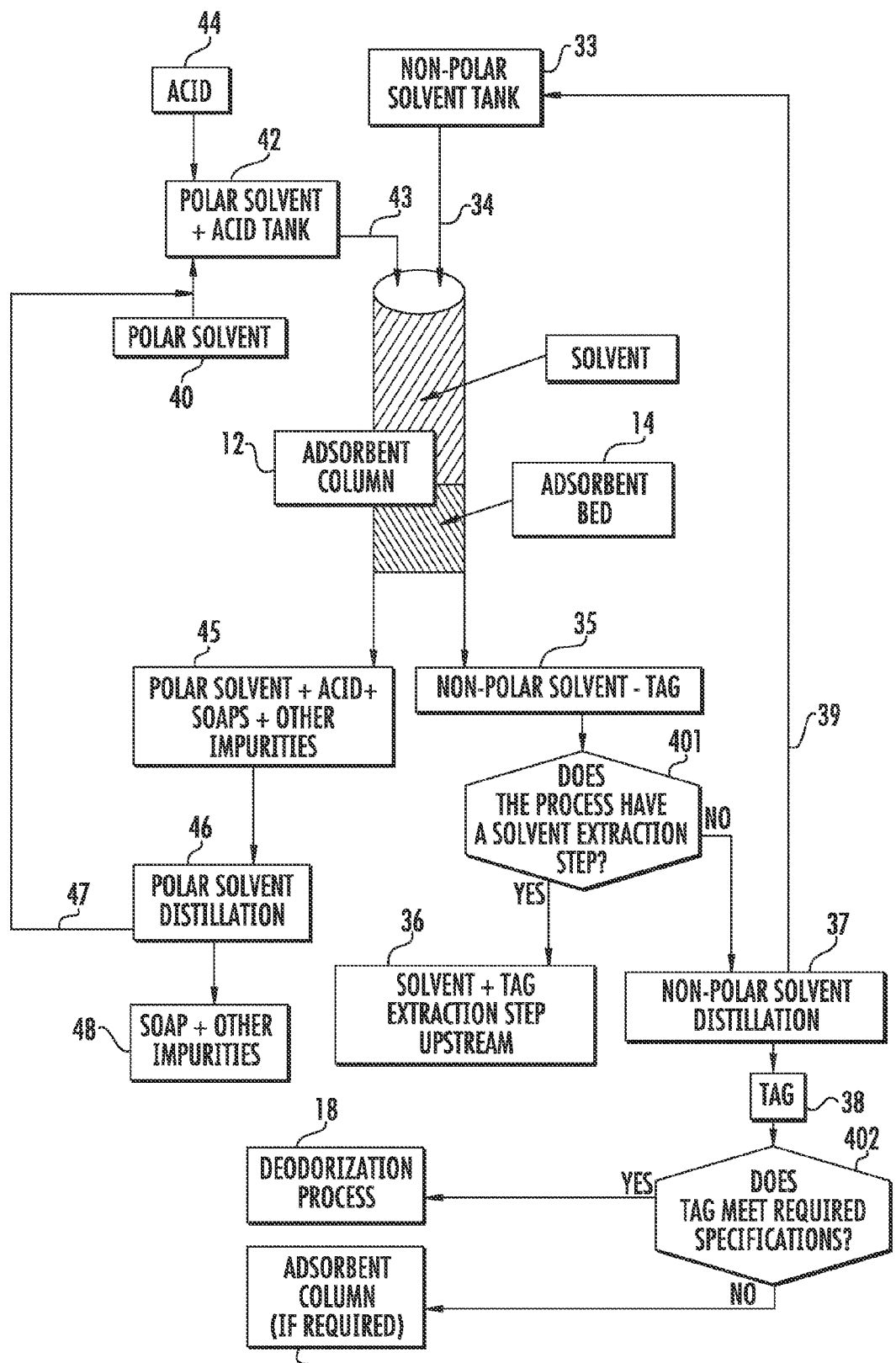
FIG. 5 is a schematic diagram of dual solvent regeneration of adsorbent in both chemical and physical refining processes with non-polar solvent and polar solvent with acid.

During regeneration in a chemical refining processes or physical refining processes shown in FIGS. 1-4, feed to adsorbent column 12 to be regenerated is stopped from adsorbent column 12 and adsorbent material 14 within adsorbent column 12 is regenerated. Non-polar solvent (NPS) 34 from non-polar solvent tank 33 is passed through adsorbent column 12 to be regenerated, as shown in FIG. 5. One suitable NPS 34 is hexane. NPS 34 is passed through adsorbent column 12 to strip absorbed TAG which is soluble in NPS 34 from adsorbent material 14. NPS and TAG mixture 35 exiting adsorption column 12 can be optionally sent to a NPS and TAG extraction step 36. Decision module 401 determines if the process includes a solvent extraction step. If the process includes an solvent extraction step, NPS and TAG mixture 35 is added upstream to the solvent extraction step (which is prior to step 20 as shown in FIG. 1-4). If the process does not include an extraction step, NPS and TAG mixture 35 is forwarded to NPS distillation 37 for reclamation of reclaimed TAG 38 and reclaimed NPS 39. Decision module 402, determines if reclaimed TAG 38 meets required parameters or specifications. If reclaimed TAG 38 meets required parameter or specifications, reclaimed TAG 38 can be forwarded to deodorization process 18. If reclaimed TAG 38 does not meet required parameters or specifications, reclaimed TAG 38 can be sent to adsorbent column 12 for reprocessing. Reclaimed NPS 39 can be reused by adding reclaimed NPS 39 to non-polar solvent tank 33.

During a second step of the regeneration of adsorbent material 14, polar solvent 40 is mixed with acid 41 in polar solvent and acid tank 42. A suitable polar solvent is an alcohol, such as methanol or ethanol. A suitable acid is sulfuric acid. Polar solvent and acid mixture 43 is passed through adsorption column 12 to remove adsorbed impurities contained in and on adsorbent material 14. Polar solvent and acid mixture 43 is passed through adsorption column 12 until such time as mixture 45 exiting adsorption column 12 contains an impurity level of zero, indicating that most if not all impurities have been stripped from the adsorbent 14 with the polar solvent solution. Mixture 45 contains the polar solvent, acid, alkyl soaps, metals, chlorophyll and other impurities. Polar solvent distillation 46 can be used for reclaiming reclaimed polar solvent 47 from soap and other impurities 48. Polar solvent distillation 46 can subject mixture 45 to heat and/or vacuum to provide reclaimed polar solvent 47. Reclaimed polar solvent 47 can be reused by adding reclaimed polar solvent 47 to polar solvent and acid tank 42.

During regeneration of a multiple column system, as shown in FIGS. 2 and 4, the first lag column 12b in the series becomes the new lead column and any subsequent lag column(s) are moved up in the order of contact in the column treatment process. Adsorbent material 14 in the original lead column is regenerated for reuse and becomes the new last lag column in the system.

Figure 6:
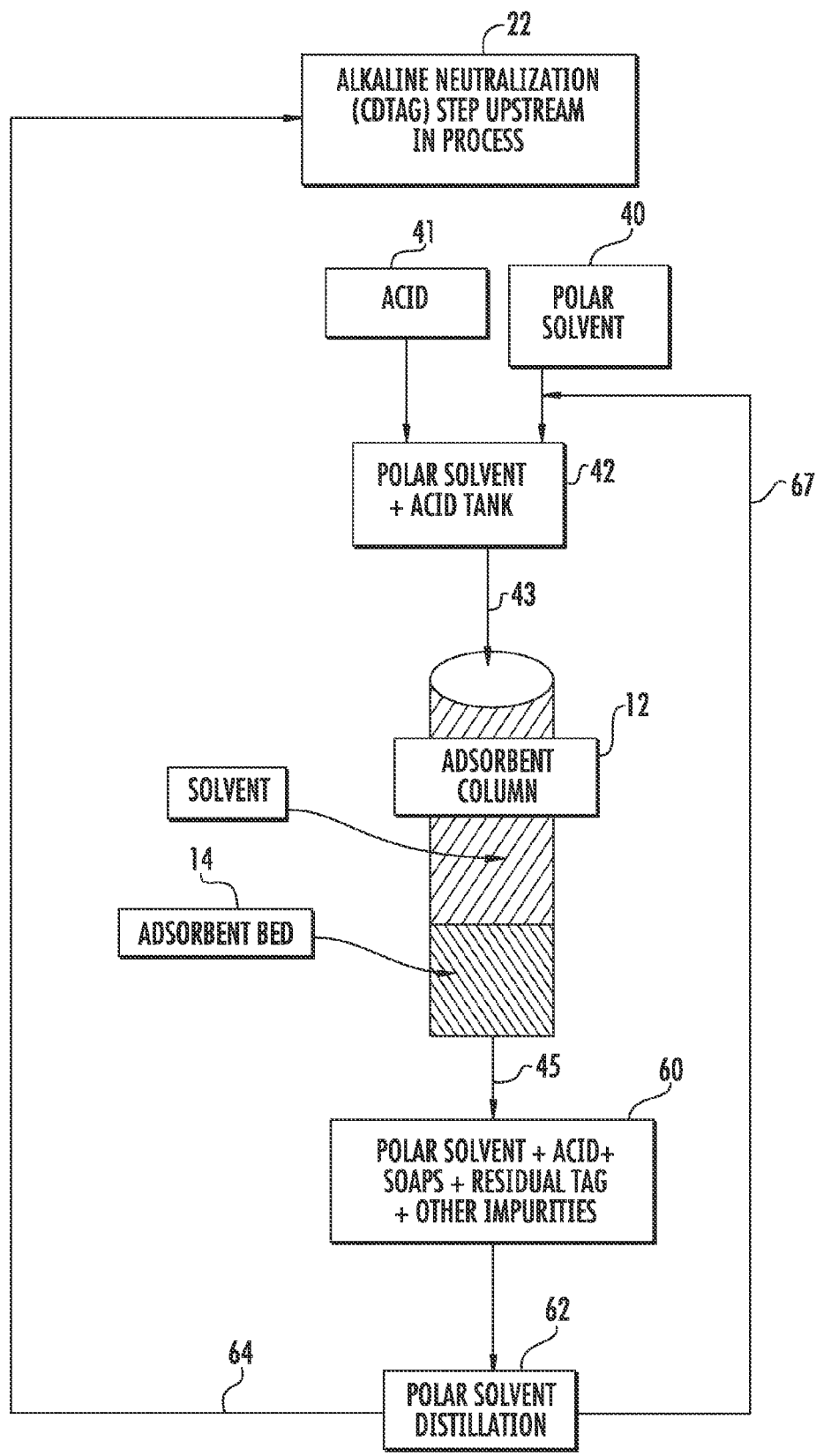
FIG. 6 is a schematic diagram of single solvent regeneration of adsorbent in a chemical refining process using a polar solvent with acid.

In an alternate embodiment, a single solvent regeneration can be used in a chemical refining process as shown in FIGS. 1-2. As shown in FIG. 6, feed to adsorbent column 12 to be regenerated is stopped from adsorbent column 12 and adsorbent material 14 within adsorbent column 12 is regenerated. Polar solvent 40 is mixed with acid 41 in polar solvent and acid tank 42. A suitable polar solvent is an alcohol, such as methanol or ethanol. A suitable acid is sulfuric acid. Polar solvent and acid mixture 43 is passed through adsorption column 12 to remove adsorbed impurities contained in and on adsorbent material 14. Polar solvent and acid mixture 43 is passed through adsorption column 12 until such time as mixture 45 exiting adsorption column 12 contains an impurity level of zero, indicating that most if not all impurities have been stripped from the adsorbent with the polar solvent solution. Mixture 60 contains the polar solvent, acid, alkyl soaps, residual TAG and other impurities. Polar solvent distillation 62 can be used for reclaiming reclaimed polar solvent 67. Polar solvent distillation 62 can subject mixture 60 to heat and/or vacuum to provide reclaimed polar solvent 67. Reclaimed polar solvent 67 can be reused by adding reclaimed polar solvent 67 to polar solvent and acid tank 42. Residual TAG and other impurities 64 can be added back upstream into the process at the point at which the alkaline solution is added to the CDTAG in step 22, as shown in FIGS. 1 and 2.

Figure 7:
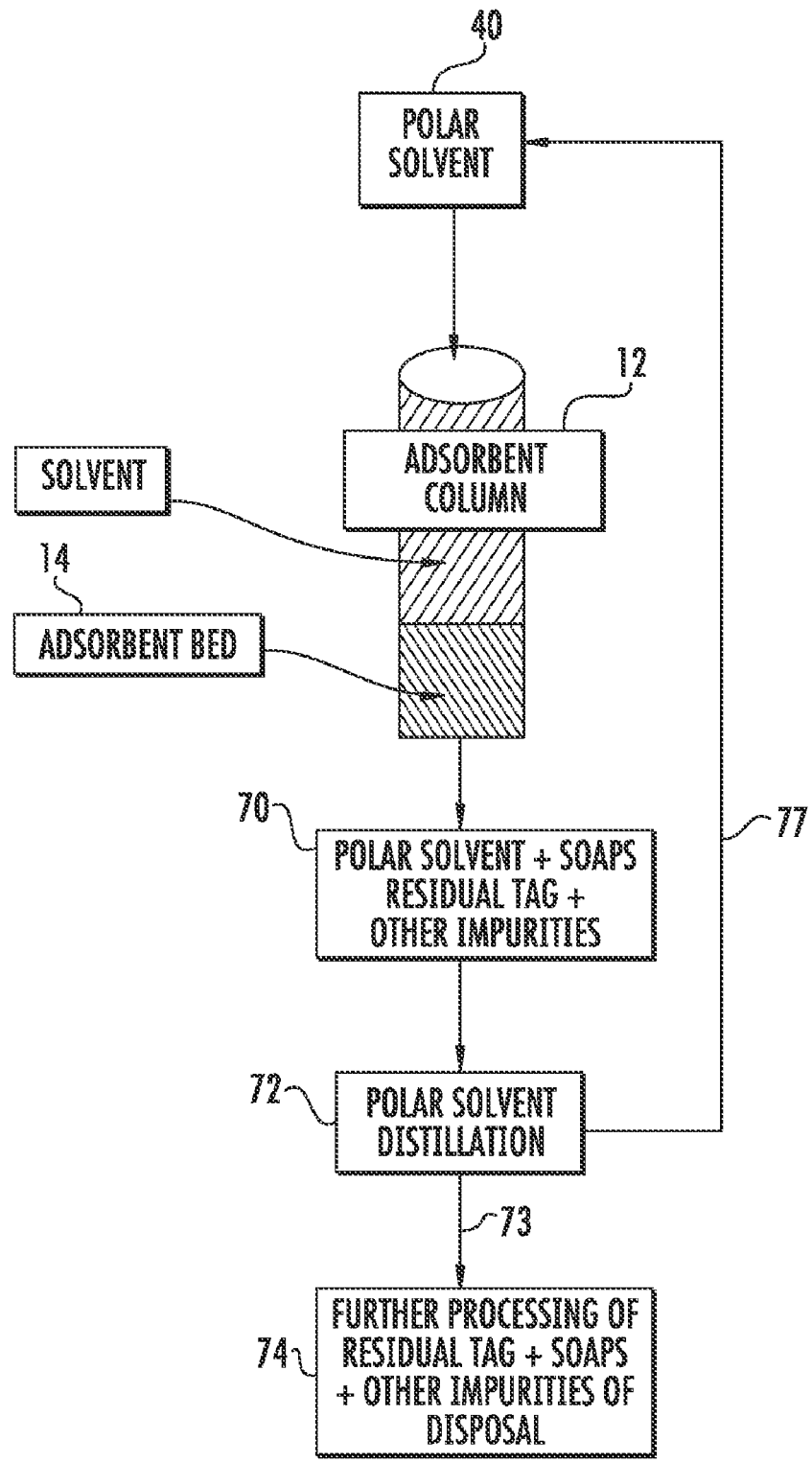
FIG. 7 is a schematic diagram of single solvent regeneration of adsorbent in a physical refining process using a polar solvent.

In an alternate embodiment, a single solvent regeneration of adsorbent can be used in a physical refining process, as shown in FIGS. 3-4. Polar solvent 40 is passed through adsorption column 12 to remove adsorbed impurities contained in and on adsorbent material 14, as shown in FIG. 7. Polar solvent 40 is passed through adsorption column 12 until such time as mixture 70 exiting adsorption column 12 contains an impurity level of zero, indicating that most if not all impurities have been stripped from adsorbent material 14 with polar solvent solution filtrate. Mixture 70 contains the polar solvent, soaps, residual TAG and other impurities. Polar solvent distillation 72 can be used for reclaiming reclaimed polar solvent 77. Polar solvent distillation 72 can subject mixture 70 to heat and/or vacuum to provide reclaimed polar solvent 77. Reclaimed polar solvent 77 can be reused by adding reclaimed polar solvent 77 to polar solvent 40. In step 74, remaining residue 73 not volatilized by distillation process 72 can be further processed or disposed of. Remaining residue 73 can include the residual TAG, soaps or other impurities.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Example 1

Dual Column Purification Using Synthetic Magnesium Silicate

ORTAG was passed through a two column system, as shown in FIG. 2 in series containing 2 g synthetic magnesium silicate (D-SOL D60 from The Dallas Group of America, Whitehouse, N.J.). Two different flow rates were tested using the same adsorbent with the same ORTAG feedstock. A summary of the results obtained from this test is shown in Table 1. The ORTAG was passed through the column until such time that the soap content of the ORTAG exiting the column was greater than 5 ppm. The initial soap concentration of the ORTAG was between 80-130 ppm.

Additionally, various samples were analyzed for chlorophyll a. These results are shown in Table 2. The initial ORTAG contained approximately 1.8 ppm Chlorophyll a.

At such time that the TAG exiting the column contained more than 5 ppm soap, the column treatment was stopped and the synthetic magnesium silicate in the lead column was regenerated, as shown in FIG. 5. A solution of hexane was first passed through the column to remove any residual TAG remaining in and on the column. After this was completed, a solution containing 0.10% sulfuric acid (93%) in ethanol was passed through the column until such time that the ethanol/sulfuric acid mixture exiting the column contained a soap value of zero.

After the regeneration of the product, the lag column became the new lead column and the regenerated lead column was placed back in series as the new lag column. Thereafter, ORTAG was passed through the column system.

TABLE 1

Summary of Column Purification Using Synthetic Magnesium Silicate
Synthetic Magnesium Silicate

| Two Columns in Series | Flow Rate = 0.35 mL/min | | | Flow Rate = 0.70 mL/min | | |
|---|---|---|---|---|---|---|
| Total Column Loading | Column Throughput (mL) | | % Treatment | Column Throughput (mL) | | % Treatment |
| 4 g | per Cycle | Cumulative | Cumulative | per Cycle | Cumulative | Cumulative |
| Initial | 4101 | 4101 | 0.108% | 7402 | 7402 | 0.060% |
| After 1st Regen. | 5513 | 9614 | 0.046% | 4803 | 12205 | 0.036% |
| After 2nd Regen. | 6733 | 16347 | 0.027% | 1265 | 13470 | 0.033% |
| After 3rd Regen. | 3590 | 19937 | 0.022% | 1600 | 15070 | 0.029% |
| AVERAGE mL | | 4984 | | | 3768 | |
| TOTAL mL | | 19937 | | | 15070 | |
| TOTAL g | | 17943 | | | 13563 | |
| % Treatment | | 0.022% | | | 0.029% | |

TABLE 2

Results for Chlorophyll Removal using Synthetic Magnesium Silicate

| Sample # | Amount through column(ml) | Chlorophyll a (ppm) |
|---|---|---|
| Initial Cycle | | |
| 1 | 100 | 0.534 |
| 11 | 1171 | 1.480 |
| 21 | 2221 | 1.560 |
| 31 | 3191 | 1.463 |
| 41 | 4196 | 1.518 |
| After 1st Regeneration | | |
| 1 | 110 | 0.372 |
| 12 | 1260 | 1.535 |
| 22 | 2270 | 1.547 |
| 32 | 3315 | 1.555 |
| 42 | 4340 | 1.582 |
| 52 | 5418 | 1.545 |
| After 2nd Regeneration | | |
| 1 | 110 | 0.763 |
| 51 | 5268 | 0.579 |
| 61 | 6333 | 0.604 |
| 70 | 7273 | 0.570 |
| After 3rd Regeneration | | |
| 1 | 95 | 0.266 |
| 10 | 1040 | 0.613 |
| 20 | 2045 | 0.594 |
| 30 | 3070 | 0.587 |
| 40 | 4090 | 0.578 |

Example 2

Single Column Purification Using Silica Gel

ORTAG was passed through a single column, as shown in FIG. 1 containing 2 g Silica Gel 60 (EMD Chemicals) at a flow rate of 0.35 mL/min. A summary of the results obtained from this product is shown in Table 3. The ORTAG was passed through the column until such time that the soap content of the ORTAG exiting the column was greater than 5 ppm. The initial soap concentration of the ORTAG was between 80-130 ppm.

Additionally, various samples were analyzed for chlorophyll a. These results are shown in Table 4. The initial ORTAG contained approximately 1.8 ppm Chlorophyll a.

TABLE 3

Summary for Single Column Purification Using Silica Gel 60

| SINGLE COLUMN | Silica Gel 60 |
|---|---|
| Column Loading | Column Throughput (mL) |
| 2 g | per Cycle |
| TOTAL mL | 1151 |
| TOTAL g | 1036 |
| % Treatment | 0.193% |

TABLE 4

Summary of Column Purification Using Silica Gel 60

| Sample # | Initial Cycle Amount through column(ml) | Chlorophyll a (ppm) |
|---|---|---|
| 1 | 120 | 0.230 |
| 11 | 1276 | 0.535 |

It is to be understood that the above described embodiments are illustrative of only a few of many possible options for regeneration which represent applications of the principles of the invention. Numerous and varied other arrangements can be readily devised in accordance with these principles by those skilled in the art without departing from the spirit and scope of the invention.

What is claimed is:

1. A process for purification of animal or vegetable oils comprising:
   (a) treating crude triacylglycerol (TAG) utilizing one or more adsorbent columns containing an adsorbent material for removing one or more impurities from the crude TAG, said TAG continuously flows through said one or more columns;
   (b) regenerating the adsorbent material with an acidic alcohol for removing adsorbed impurities from the adsorbent material; and
   (c) reusing the adsorbent material in step (a),
   wherein said impurities are comprised of one or more of phosphorus, soap, metals, free fatty acids (FFA), flavor compounds, odor compounds, color bodies, chlorophyll and other impurities that reduce the stability of finished TAG.

2. The process of claim 1 wherein said crude triacylglycerol is degummed (CDTAG).

3. The process of claim 1 wherein the adsorbent material is a powder, granulated, extruded, or otherwise processed to facilitate flow through the one or more columns.

4. The process of claim 1 wherein the adsorbent material is selected from carbon, silica, zeolite, metal silicate, metal oxide, bleaching clay, and acid activated bleaching clay.

5. The process of claim 1 wherein the adsorbent material is magnesium silicate.

6. The process of claim 1 wherein the adsorbent is synthetic magnesium silicate.

7. The process of claim 1 wherein the adsorbent is silica gel.

8. The process of claim 1 wherein the adsorbent is activated alumina.

9. The process of claim 1 wherein the adsorbent is bleaching clay.

10. The process of claim 1 wherein the adsorbent is acid activated bleaching clay.

11. The process of claim 1 wherein the regeneration of the adsorbent material is performed in a first step with a first solvent and a second step with a second solvent, wherein the second solvent is the acidic alcohol.

12. The process of claim 11 wherein said TAG absorbed in the adsorbent material removed from the adsorbent material in the first step with the first solvent.

13. The process of claim 12 wherein the first solvent is a non-polar solvent.

14. The process of claim 13 wherein the first solvent is hexane.

15. The process of claim 1 wherein the acid is sulfuric acid.

16. The process of claim 1 wherein the alcohol is ethanol.

17. The process of claim 1 wherein the alcohol is methanol.

18. The process of claim 12 wherein the first solvent is separated from a mixture of the first solvent and TAG removed from the adsorbent material during the regeneration, said first solvent is reclaimed for reuse and the TAG separated from the mixture of the first solvent and the TAG is further processed.

19. The process of claim 18 wherein the first solvent is separated from the mixture using distillation.

20. The process of claim 12 wherein the mixture of the first solvent and the TAG removed from the adsorbent during regeneration is recycled back upstream and mixed into a solvent and TAG mixture from oil extraction from an oil seed step.

21. The process of claim 12 wherein the first solvent is separated from a filtrate of the first solvent and TAG and, the first solvent is reclaimed for reuse.

22. The process of claim 21 the first solvent is separated from the filtrate of the first solvent and TAG using distillation.

23. The process of claim 22 wherein the TAG remaining after the first solvent is separated from the filtrate of the first solvent and TAG is further processed.

24. The process of claim 11 wherein the second solvent is separated from a filtrate of the second solvent and impurities from regeneration and the second solvent is reclaimed for reuse.

25. The process of claim 24 wherein the second solvent is separated from the impurities of the filtrate of the second solvent and impurities using distillation.

26. The process of claim 24 wherein the impurities remaining after the second solvent is separated from the filtrate of the second solvent and impurities is further processed or disposed of.

27. The process of claim 1 wherein the regeneration of the adsorbent material is performed in one step.

28. The process of claim 1 wherein the acidic alcohol is separated from a filtrate of the acidic alcohol, the TAG, and the impurities and the acidic alcohol is reclaimed for reuse.

29. The process of claim 28 wherein the acidic alcohol is separated from the filtrate of the acidic alcohol, the TAG, and the impurities using distillation.

30. The process of claim 28 wherein residual filtrate after separation of the acidic alcohol from the filtrate is recycled back upstream and blended with the crude TAG, and further comprising an alkaline neutralization step of the crude TAG.

31. The process of claim 30 wherein the crude TAG is separated from impurities by centrifugation.

32. The process of claim 31 wherein residual impurities are centrifuged out into soap stock.

33. The process of claim 1 wherein the acidic alcohol is entrained in TAG flowing from the regenerated column and is separated from the TAG and reclaimed for reuse.

34. The process of claim 33 wherein the separation of the solvent from the TAG is performed in a deodorization step.

35. The process of claim 33 wherein the separation of the solvent from the TAG is performed in by the step of evaporation of the solvent from the TAG prior to the deodorization step.

36. The process of claim 35 wherein the TAG is sent to a deodorization step of the process for purification of animal and vegetable oils.

* * * * *